United States Patent [19]

Igarashi et al.

[11] Patent Number: 5,841,000
[45] Date of Patent: Nov. 24, 1998

[54] PROCESS FOR PRODUCING TRANS-2 BROMOINDAN-1-OL

[75] Inventors: Yoshio Igarashi; Shigeru Nakano; Yuzi Konno; Fumihiro Asano, all of Fukushima-ken, Japan

[73] Assignee: Ichikawa Gosei Chemical Co., Ltd., Tokyo, Japan

[21] Appl. No.: 894,886

[22] PCT Filed: Mar. 13, 1996

[86] PCT No.: PCT/JP96/00619

§ 371 Date: Nov. 19, 1997

§ 102(e) Date: Nov. 19, 1997

[87] PCT Pub. No.: WO96/28406

PCT Pub. Date: Sep. 19, 1996

[30] Foreign Application Priority Data

Mar. 14, 1995 [JP] Japan .................................. 7-054213

[51] Int. Cl.$^6$ ........................... C07C 33/34; C07C 22/00
[52] U.S. Cl. ........................... 568/808; 570/183
[58] Field of Search ................... 568/808, 815, 568/715, 817; 570/181, 183

[56] References Cited

FOREIGN PATENT DOCUMENTS

| 0 658 537 | 6/1995 | European Pat. Off. . |
| 7-316106 | 12/1995 | Japan . |

OTHER PUBLICATIONS

L. Benmenni, "Acta Cryst. Sec. C" vol. 50 (1994), pp. 1636–1638.

A. Gagis, "J. Org. Chem." vol. 37, No. 20 (1972), pp. 3181–3182.

Dale F. Shellhamer, "J. Chem. Soc. Perkin Trans 2" (1991), pp. 401–403.

T. Ho, "Synthesis" (1977), pp. 675–677.

W.E. Billups, "J. Org. Chem." vol. 45, No. 23 (1980), pp. 4636–4641.

G.E. Heasley, "J. Org. Chem." vol. 45, No. 23 (1980), pp. 5150–5155.

M.R. Detty, "J. Am. Chem. Soc." vol. 118, No. 2, Jan. 17, 1996 (17 Jan. 1996), pp. 313–318.

D.T. Sawyer, "J. Am. Chem. Soc." vol. 117, No. 1, Jan. 11, 1995 (11 Jan. 1995), pp. 106–109.

*Primary Examiner*—Michael L. Shippen
*Assistant Examiner*—Karl J. Puttlitz, Jr.
*Attorney, Agent, or Firm*—Frommer Lawrence & Haug, LLP

[57] ABSTRACT

A cheap industrial method for making trans-2-bromoindan-1-ol. Trans-2-bromoindan-1-ol represented by Formula (II) is made by hydrolysing 1,2-dibromoindane represented by General Formula (I) (where the configuration of the bromine atoms on position 1 and position 2 can be trans or cis, or it can be a mixture of trans and cis isomers). Trans-2-bromoindan-1-ol represented by Formula (II) can also be made by brominating indene to synthesize 1,2-dibromoindane, and then continuously hydrolysing this 1,2-dibromoindane without isolating it. 1,2-Dibromoindane can also be made by reacting indene with hydrogen bromide in the presence of hydrogen peroxide.

20 Claims, No Drawings

PROCESS FOR PRODUCING TRANS-2 BROMOINDAN-1-OL

TECHNICAL FIELD

The present invention relates to an industrially useful method for making trans-2-bromoindan-1-ol.

BACKGROUND ART

Trans-2-bromoindan-1-ol is a pharmaceutical intermediate for anti-HIV drugs, etc., and is useful as a starting material for making cis-1-aminoindan-2-ol. For example, in Japanese Patent Application 6-298619 which is a previous patent by the present applicants, it is stated that cis-1-aminoindan-2-ol can be obtained by reacting trans-2-bromoindan-1-ol under acid conditions with acetonitrile to give trans-1-(acetamide)-2-bromoindane, cyclizing this to make a cis-oxazoline derivative, and then hydrolysing. Similarly, in the method of Gagis et al. (*J. Ore. Chem.* 37, 3181 (1972)) cis-1,2-epoxyindane is obtained by treating trans-2-bromoindan-1-ol under basic conditions. In the aforementioned Japanese Patent Application 6-298619 it is shown that a derivative of cis-oxazoline is produced by reacting this epoxy compound under acid conditions with acetonitrile, and that cis-1-aminoindan-2-ol can be obtained by hydrolysing this.

To date, various methods have been disclosed for making trans-2-bromoindan-1-ol. For example, Porter et al. (*J. Am. Chem. Soc.* 57, 2022 (1935)) obtained trans-2-bromoindan-1-ol by reacting bromine water with indene; however, the yield was low at 31%. Similarly, Suter et al. (*J. Am. Chem. Soc.* 62, 3473 (1940)) obtained trans-2-bromoindan-1-ol with 94% yield by saturating an aqueous solution of sodium bromide with bromine and then reacting with indene in the presence of a large quantity of a dispersant. This method gives a comparatively good yield but efficiency is poor, and using a 5-litre reaction vessel only 204 g of the intended product is obtained. Moreover, there are industrial problems in that a large quantity of reaction mother liquor is produced, and the fact that the mother liquor is a mixture of sodium bromide and hydrogen bromide complicates treatment after the reaction. On the other hand, Guss et al. (*J. Am. Chem. Soc.* 77, 2549 (1955)) obtained trans-2-bromoindan-1-ol with a yield of 59% by reacting N-bromosuccinimide with indene in water at room temperature for 3 hours. Although this method is comparatively efficient, from the economic point of view N-bromosuccinimide needs to be regenerated by separating out by-product succinimide and then brominating.

As indicated above, no industrial and cheap method is known for making trans-2-bromoindan-1-ol.

DISCLOSURE OF THE INVENTION

The present invention offers an industrial and cheap method for making trans-2-bromoindan-1-ol.

It has been disclosed by Dalton et al. (*J. Am. Chem. Soc.* 90, 5498 (1968)) that when an alkene is brominated in water bromine cations attack the carbon-carbon double bond to produce a bromonium cation intermediate, and this intermediate is attacked by solvated anions ($OH^-$ anions in the case of a reaction in water) to produce a bromhydrin.

Thus, it is suggested that all of the prior art cited above includes this reaction mechanism. In the reaction of bromine water and indene of Porter et al., for example, $Br^+OH^-$ (produced by an equilibrium reaction between bromine and water) contained in the bromine water becomes the reaction reagent; a bromonium cation intermediate is first produced by $Br^+$ attacking indene, and then trans-2-bromoindan-1-ol (indenebromohydrin) is produced by the action of $OH^-$. However, because the concentration of $Br^+OH^-$ in water is small the yield is low. Similarly, Suter et al. dissolved bromine in sodium bromide in order to increase the concentration of $Br^+OH^-$ in the water. Moreover, Guss et al. used the reaction of indene with $Br^+OH^-$ generated from water and N-bromosuccinimide.

The present inventors have perfected the present invention as the result of pursuing concerted studies focusing on the importance of the concentration of bromonium cations produced as an intermediate stage of the synthesis of trans-2-bromoindan-1-ol.

There are 2 methods for generating bromonium cations in an indene system:

1) Removal of the substituent group from the 1 position of a 1-(substituted)-2-bromoindane derivative, and
2) $Br^+$ attack of indene.

The present investigators first pursued studies on method 1).

It is it known that when the substituent group on position 1 of the indane skeleton is a hydroxyl group it can be easily removed under acid conditions to produce a carbocation. For example, Suter et al. (*J. Am. Chem. Soc.* 62, 3473 (1940)) reported that cis/trans isomerization is produced by heating indane-1,2-diol or 2-chloro-1-indanol in an acid aqueous solution, and this shows that a hydroxyl group on position 1 is removed to produce a carbocation intermediate (equation below).

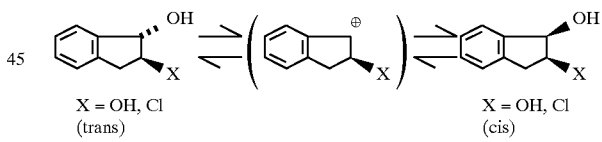

X = OH, Cl           X = OH, Cl
(trans)                          (cis)

The present inventors have also discovered that trans-1-acetamide-2-bromoindane is produced by reacting trans-2-bromoindan-1-ol with acetonitrile under acid conditions (Japanese Patent Application 6-298619), and this indicates that acetonitrile attacks the carbocation produced by the removal of the hydroxyl group on position 1 (equation below).

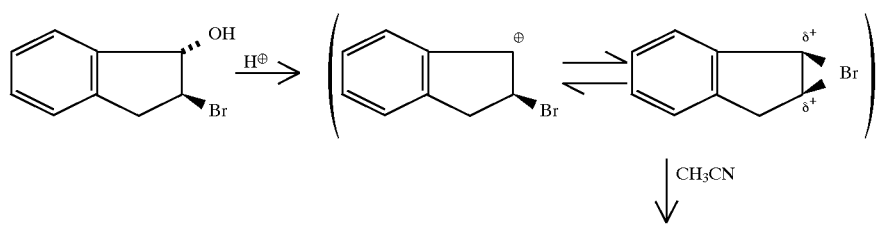

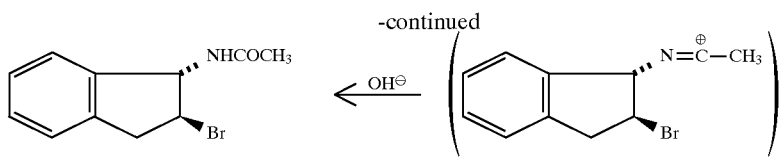

The present inventors have also discovered that this reaction is also possible when 1,2-dibromoindane is used. Thus, this results shows that under selected conditions a bromonium cation is produced by withdrawal of a bromine atom on position 1 of 1,2-dibromoindane (equation below).

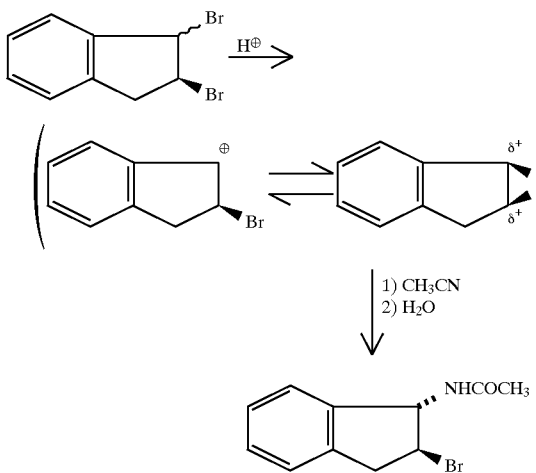

As the result of investigations based on the results above, the present inventors have discovered that trans-2-bromoindan-1-ol represented by Formula (II)

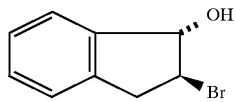 (II)

can be obtained easily by hydrolysing 1,2-bromoindane represented by General Formula (I)

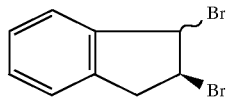 (I)

(where the bromine atoms on position 1 and position 2 in the formula can be in cis configuration or trans configuration or a mixture of these) under selected conditions.

The present invention is explained in detail below.

The 1,2-dibromoindane starting material can be the cis or trans isomer or a mixture of these. 1,2-Dibromoindane can be obtained by reacting indene with bromine in a suitable solvent. For example, Billups et al. (*J. Ore. Chem.* 44, 4218 (1979)) obtained 1,2-dibromoindane by brominating indene in ether. It is also known that the ratio of cis-1,2-dibromoindane and trans-1,2-dibromoindane produced in the bromination reaction depends on the reaction solvent. Heasley et al. (*J. Org. Chem.* 45, 5150 (1980)) have reported the percentages of the cis and trans isomers when bromination of indene was performed in different solvents. In the present invention, either isomer can be employed as starting material because no matter which is used the bromonium cation intermediate is produced by the removal of the bromine atom on position 1.

1,2-dibromoindane is converted to the desired trans-2-bromoindan-1-ol by mixing in water. The reaction temperature is preferably room temperature to 100° C., and more preferably 50°–80° C. When the temperature is lower than this the reaction progresses slowly, and when the temperature is higher than this the yield is lowered because the intended product trans-2-bromoindan-1-ol is converted to indan-1-one and/or indan-2-one via cis-2-bromoindan-1-ol produced by isomerization (equation below).

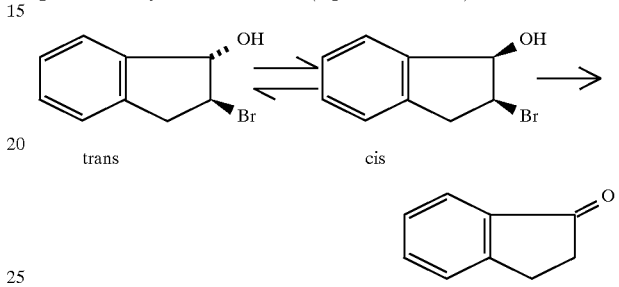

When this hydrolysis is performed in a non-uniform system of water and 1,2-dibromoindane, which is sparingly soluble in water, a high stirring efficiency is preferred. An emulsion is preferably further formed in order to cause full contact between the organic layer and aqueous layer, and the addition of dispersants and/or emulsifiers is an effective measure. Dispersants and/or emulsifiers which can be employed include glyceryl fatty acid esters, sucrose fatty acid esters, sorbitan fatty acid esters, propylene glycol fatty acid esters and polyoxyethylene ethers; polyoxyethylene (10) octyl phenyl ether (trade name : Triton X-100) is ideal. The quantity of dispersant and/or emulsifier employed is preferably 0.5–10 wt % relative to 1,2-dibromoindane, and 1 wt % to 5 wt % is more preferable. If the quantity of dispersant and/or emulsifier employed is smaller than this an adequate dispersing/emulsifying effect is not obtained, and more than this is economically disadvantageous.

Also, because water-insoluble trans-2-bromoindan-1-ol separates out as the hydrolysis reaction progresses, it can be performed in the presence of an aprotic organic solvent in order to obtain an adequate stirring effect. When for example a solvent is employed which is insoluble in water or sparingly soluble in water, the reaction system becomes non-uniform and therefore as previously mentioned a dispersant and/or emulsifier is preferably used. Solvents which can be employed include chlorinated solvents such as dichloromethane, dichloroethane, chloroform, carbon tetrachloride, chlorobenzene and dichlorobenzene, etc., and hydrocarbons such as hexane, heptane, octane, benzene, toluene and xylene, etc. The quantity of these solvents employed can be decided in the light of phase solubility with the 1,2-dibromoindane starting material and the solubility of the intended trans-2-bromoindan-1-ol. Moreover, this reaction is preferably performed at 50°–80° C., and therefore when the boiling point of the solvent or azeotropic mixture of solvent and water at ordinary pressure is lower than the preferred reaction temperature it can be performed at increased pressure. The preferred solvents are chlorobenzene and dichloroethane, and more preferably chlorobenzene. Excess 1, 2-dibromoindane can also be employed (i.e. the starting material can be employed as a solvent).

This hydrolysis reaction can also be performed in the presence of a solvent which dissolves water, 1,2-dibromoindane and trans-2-bromoindan-1-ol. When the quantity of solvent employed is small the reaction system becomes non-uniform, but a uniform reaction is possible by selecting the quantity of solvent. Solvents which can be employed include acetone, ethyl methyl ketone, dimethylformamide, dimethyl sulphoxide, N-methylpyrrolidone and 1,3-dimethyl-2-imidazolidinone, etc. In this case the reaction can be performed under a reaction pressure which will allow a suitable reaction temperature.

The velocity of the hydrolysis of 1,2-dibromoindane differs depending on pH, and it is preferably performed at a lower pH. This is not a problem, since hydrogen bromide is produced as a by-product as the hydrolysis progresses, and consequently the pH decreases steadily; however, when the pH at the beginning of hydrolysis is comparatively high in the acid region the system pH is preferably set low.

The progress of the reaction can be followed by gas chromatography (GC) or liquid chromatography (HPLC), and consequently the end of the reaction can be decided from the quantity of 1,2-dibromoindane left and the quantity of trans-2-bromoindan-1-ol produced. The time required for the hydrolysis of 1,2-dibromoindane differs with the reaction temperature, the use or otherwise of a dispersant, the use or otherwise of an aprotic solvent and the quantity of water added, and therefore the reaction is preferably followed by the aforementioned methods.

The 1,2-bromoindane starting material can further be hydrolysed continuously with its synthesis without isolating it, to obtain the desired trans-2-bromoindan-1-ol. In this case, 1,2-dibromoindane can be synthesized by reacting indene and bromine in the presence or not in the presence of an aprotic solvent which does not cause bromination, and this can be hydrolysed under the aforementioned conditions by adding the desired quantity of water; or indene can be brominated while it is dispersed in water to synthesize 1,2-dibromoindane, and this can be hydrolysed in the presence or not in the presence of an aprotic solvent which does not cause bromination. In the case of the latter method, by selecting the reaction conditions the production and hydrolysis of 1,2-dibromoindane can be performed in parallel. In addition, by performing bromination employing excess indene (i.e. using indene as an aprotic solvent) it is possible to synthesize 1,2-dibromoindane, and perform hydrolysis and synthesize trans-2-bromoindan-1-ol in the presence of unreacted indene. Hydrogen bromide is a by-product of the hydrolysis of 1,2-dibromoindane, and addition of hydrogen bromide to indene in the hydrolysis of 1,2-dibromoindane can be suppressed by selecting the reaction conditions.

The isolation of the intended substance after the end of the reaction will differ depending on whether or not an aprotic solvent is used, and the quantity employed.

For example, when the reaction is performed without using aprotic solvent the product separates from water, and after solid separation ordinary clean-up methods can be used. However, when a product including oily by-products is filtered or centrifuged as it stands the yield of the desired trans-2-bromoindan-1-ol is lowered because it dissolves in the oily substances in the filtrate. Consequently, after ending the reaction an organic solvent in which trans-2-bromoindan-1-ol is comparatively sparingly soluble and the by-products are readily soluble is preferably added at a suitable temperature, and the intended product dispersed in the organic solvent is subjected to solid separation after removing the aqueous layer. In this process dichloromethane, dichloroethane and chlorobenzene, etc., can be used as an organic solvent. Or trans-2-bromoindan-1-ol can be extracted at a suitable temperature with an organic solvent in which it is highly soluble, and then collected by crystallization by an ordinary method. Ethyl acetate, propyl acetate and isopropyl acetate, etc., can be used as the extracting solvent.

On the other hand, when the reaction is performed using an aprotic solvent the following treatment can be carried out. When a solvent is employed in which the solubility of trans-2-bromoindan-1-ol is comparatively small, solid separation of the intended product dispersed in the organic layer can be performed after removing the aqueous layer as described above. When a solvent is employed in which the solubility of trans-2-bromoindan-1-ol is comparatively large, if crystallization of the intended product is noticeable the mother liquor can be concentrated after isolating these crystals, and the intended product can be crystallized by an ordinary method.

The present inventors next investigated the production of the indenebromonium cation intermediate by bromo cation ($Br^+$) attack of indene.

It is known that $Br^+OH^-$ and $Br_2$ are produced by reaction between hydrogen peroxide and hydrogen bromide and that this reaction system has an equilibrium ((Jolles (editor) "*Bromine and its compounds.*" p. 100 (1966) (equations below).

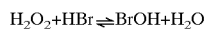

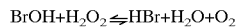

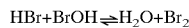

The present inventors have perfected the present invention as the result of pursuing concerted studies on the possibility that if $Br^+$ was generated by reacting excess hydrogen peroxide and hydrogen bromide in the presence of indene, 1,2-dibromoindane could be produced when the opposing anion was Br and the desired trans-2-bromoindan-1-ol could be synthesized when the opposing anion was $OH^-$, with the discovery that 1,2-dibromoindane and trans-2-bromoindan-1-ol are indeed produced.

The present invention will be explained in concrete terms.

Hydrogen peroxide is preferably employed at 0.5–1.2 mols per mol of indene. Hydrogen bromide is preferably employed at 0.5–2.2 mol per mol of indene.

Because hydrogen bromide is needed at 2 mol equivalent of indene in order to produce 1,2-dibromoindane, the maximum quantity produced is 0.5 mol equivalent of indene; and because hydrogen bromide is needed at 1 mol equivalent of indene for the production of trans-2-bromoindan-1-ol the maximum quantity produced is 1 mol equivalent of indene (equations below).

(Production of 1,2-dibromoindane)
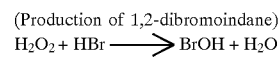

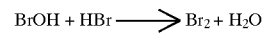

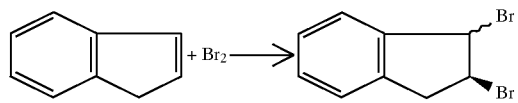

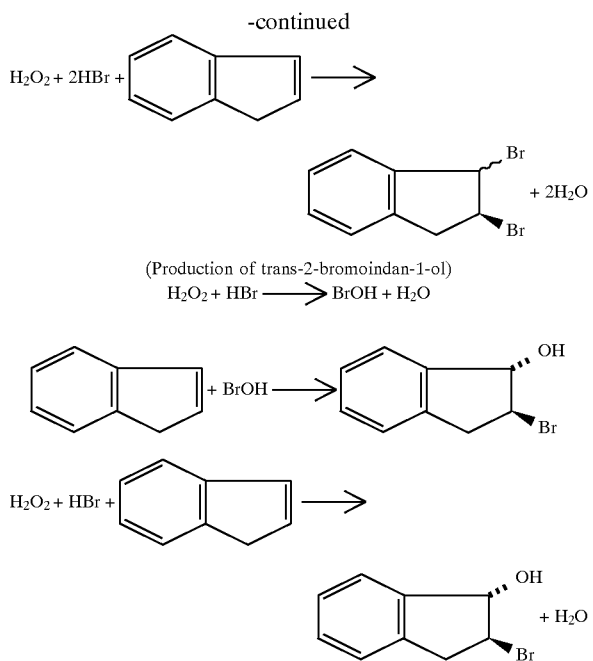

In this case, the proportions of 1,2-dibromoindane and trans-2-bromoindan-1-ol produced will change depending on the reaction temperature, the pH of the reaction system and the quantity of water (or concentration of hydrogen bromide in the water). Thus, the reaction temperature and pR affect the velocity of 1,2-dibromoindane hydrolysis: when the reaction temperature is preferably $\leq 0°$ C. and more preferably $-10°$ C., and the pH is preferably $\geq 0.0$ and more preferably $\geq 1.0$, the ratio produced becomes almost those of the indene addition reactions; and when the temperature is higher or the pH is lower 1,2-dibromoindane hydrolysis is produced in parallel with the addition of $Br_2$ or BrOH to indene, and consequently the proportion of trans-2-bromoindan-1-ol produced becomes larger. In addition, because there is an equilibrium in the hydrogen bromide and hydrogen peroxide reaction system, the quantity of water (or the hydrogen bromide concentration in the water) affects the percentages of $Br_2$ and BrOH produced in the reaction system and therefore as a result is related to the proportions of the products of addition reaction. Thus, by selecting appropriate reaction conditions it is possible to control the ratio of 1,2-dibromoindane and trans-2-bromoindan-1-ol. When 1,2-dibromoindane is desired a low reaction temperature, a pH comparatively high in the region 0–7 and little water in the reaction system (i.e. a large concentration of hydrogen bromide in water) are preferred; and when trans-2-bromoindan-1-ol is desired a comparatively high reaction temperature, a low pH $\leq 0$ and a large quantity of water in the reaction system (i.e. a small concentration of hydrogen bromide in water) are preferred. When trans-2-bromoindan-1-ol is desired, trans-2-bromoindan-1-ol also can be obtained by hydrolysing the 1,2-dibromoindane in the mixture, by treating the mixture as previously described, in the previously described preferred conditions in the presence of water. At the same time by-product hydrogen bromide reacts with the remaining hydrogen peroxide, and finally produces trans-2-bromoindan-1-ol.

When the present reaction is performed in the presence of water in a non-uniform liquid phase to give trans-2-bromoindan-1-ol, the stirring efficiency is preferably high, because the brominating reagent is in the aqueous layer and the indene is in the oil layer. Moreover, an emulsion is preferably formed in order to bring the organic layer and aqueous layer into adequate contact, and dispersants and/or emulsifiers become efficacious. Dispersants and/or emulsifiers which can be employed include glyceryl fatty acid esters, sucrose fatty acid esters, sorbitan fatty acid esters, propylene glycol fatty acid esters and polyoxyethylene ethers, etc.; and polyoxyethylene(10) octyl phenyl ether (trade name: Triton X-100) is ideal. The quantity of dispersant and/or emulsifier employed is preferably 0.5–10 wt %, and more preferably 1 to 5 wt %, relative to indene. When the quantity of dispersant and/or emulsifier employed is less than this an adequate dispersing/emulsifying effect is not obtained, and more than this is economically disadvantageous.

Water-insoluble trans-2-bromoindan-1-ol separates out when this reaction is performed in the presence of water, and consequently it can be performed in the presence of an aprotic organic solvent in order to get an adequate stirring effect. Because the reaction system becomes non-uniform when a solvent insoluble or sparingly soluble in water is employed, a dispersant and/or emulsifier such as those described previously is ideally employed. Solvents which can be employed include chlorinated solvents such as dichloromethane, dichloroethane, chloroform, carbon tetrachloride, chlorobenzene and dichlorobenzene, etc., and hydrocarbons such as hexane, heptane, octane, benzene, toluene and xylene, etc. It is also possible to perform the addition reactions under conditions for 1,2-dibromoindane hydrolysis. In this event the reaction temperature is preferably 50°–80° C., and therefore it can be performed under increased pressure when the boiling point of the solvent or azeotropic mixture of water and solvent at ordinary pressure is lower than the preferred reaction temperature. The preferred solvents are chlorobenzene and dichloroethane, and chlorobenzene is more preferred.

On the other hand this reaction can be performed in the presence of a solvent which dissolves water, indene and trans-2-bromoindan-1-ol. When the quantity of solvent employed is small the reaction system becomes non-uniform, but a uniform reaction is possible by selecting the quantity of solvent. Solvents which can be employed include dimethylformamide, dimethyl sulphoxide, N-methylpyrrolidone and 1,3-dimethyl-2-imidazolidinone, etc. In this case the reaction can be performed under a reaction pressure which will allow a suitable reaction temperature.

As described previously, the present reaction is efficacious in synthesizing 1,2-dibromoindane by reacting indene and bromine, and then hydrolysing this 1,2-dibromoindane in a continuous process. Thus, because hydrogen bromide is a by-product in the hydrolysis of 1,2-dibromoindane, the desired trans-2-bromoindan-1-ol can be made continuously by adding an almost equimolar quantity of indene to the hydrogen bromide in the reaction mixture, and bringing about the action of the hydrogen bromide and an almost equimolar quantity of hydrogen peroxide.

Moreover, continuous manufacture from indene is possible. For example, the process below is possible. Firstly 1 mol of 1,2-dibromoindane is produced by adding 1 mol of bromine to 2 mol of indene in the presence or in the absence of water (Equation (1) below).

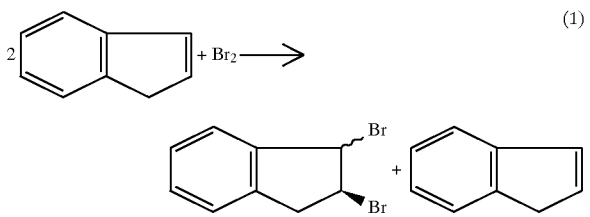

Then 1 mol of trans-2-bromoindan-1-ol and 1 mol of hydrogen bromide are produced by progressive hydrolysis of 1,2-dibromoindane by heating and stirring in the presence of water (Equation 2 below).

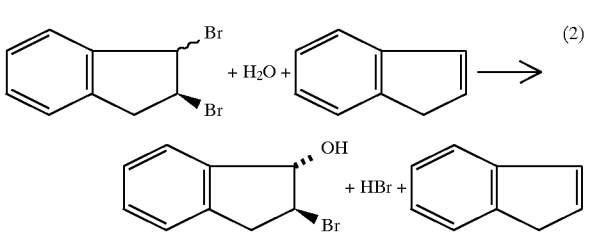

Finally 1 mol of hydrogen peroxide is added to bring about the production of trans-2-bromoindan-1-ol or 1,2-dibromoindane, and when 1,2-dibromoindane is produced this can be hydrolysed at a set temperature to produce trans-2-bromoindan-1-ol (Equation 3 below).

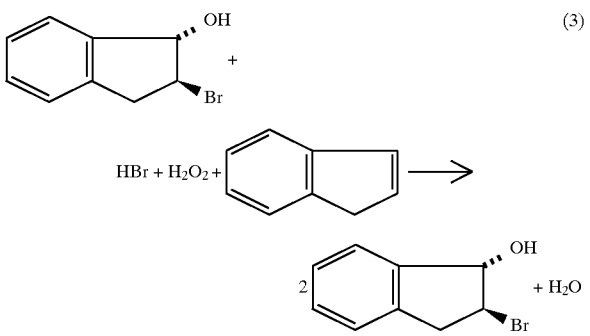

Overall, 2 mol of 2-trans-2-bromoindan-1-ol are produced by employing 2 mol of indene and 1 mol each of bromine and hydrogen peroxide (Equation 4 below).

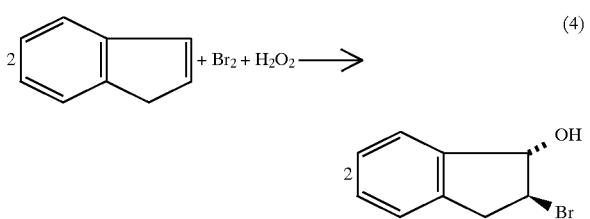

The optimum forms for carrying out the invention

The invention is explained in even more detail below by means of embodiments.

Embodiment 1

Synthesis of trans-2-bromoindan-1-ol (II) by hydrolysis of 1,2-dibromoindane (I) (added dispersant)

50 ml of water, 5.0 g of 1,2-dibromoindane (trans: cis= 84:16; 0.18 mol) and 0.2 g of Triton X-100 were put into a 100-ml 3-mouthed flask, and were emulsified by stirring together with a magnetic stirrer. Mixing was continued for 6 hours at 50°–60° C. Soft yellow semi-crystalline particles precipitated. By cooling to room temperature, filtering at decreased pressure and then washing with water, 4.26 g of moist crude crystals were obtained. These were dispersed in 10 ml of dichloromethane, and washed by mixing at 0° C. The crystals were filtered at decreased pressure, followed by washing with a small quantity of dichloromethane (0° C.) and then drying, to obtain 2.64 g of pale yellow crystals of trans-2-bromoindan-1-ol (yield 68.4%; HPLC purity 96.5%).

Embodiment 2

Synthesis of trans-2-bromoindan-1-ol (II) by hydrolysis of 1,2-dibromoindane (continuous synthesis from bromination of indene, use of equimolar quantities of indene and bromine, added dispersant)

50 ml of water, 2.44 g of indene (content 95 wt %; 0.02 mol) and 0.2 g of Triton X-100 were put into a 100-ml 3-mouthed flask and emulsified by stirring together with a magnetic stirrer. At 50–60° C., 3.2 g of bromine (0.02 mol) was added dropwise, followed by mixing at the same temperature for 6 hours. The semicrystalline precipitate was collected by filtration and treated as in Embodiment 1, to obtain 2.89 g of pale yellow crystals of trans-2-bromoindan-i-ol (yield based on indene 67.8%; HPLC purity 97.2%).

Embodiment 3

Synthesis of trans-2-bromoindane-1-ol (II) by indene-hydrogen bromide-hydrogen peroxide reaction (added dispersant)

237 ml of water, 173.9 g of indene (92 wt %; 1.38 mol), 2.8 g of Triton X-100 and 262.0 g of hydrogen bromide (47 wt %; 1.52 mol, 1.1 mol/mol indene) were put into a 1000-ml 3-mouthed flask, and emulsified by stirring together with a magnetic stirrer. The emulsion was stirred at 60° C. as 147.2 g of hydrogen peroxide (35 wt %; 1.52 mol, 1.1 mol/mol indene) was added dropwise over 4 hours and 20 minutes. After stirring for 2 hours at the same temperature, stirring was continued at room temperature overnight. 200 ml of dichloromethane was added to the reaction mixture, and after stirring at room temperature for 1 hour it was filtered at decreased pressure. The wet crystals were dried, to obtain 246.1 g of pale yellow crystals of trans-2-bromoindan-1-ol (yield 83.9%; GC purity 97.0%).

Embodiment 4

Synthesis of trans-2-bromoindan-1-ol (II) by hydrolysis of 1,2-dibromoindane (I) (continuous synthesis from bromination of indene, employment of excess indene, added dispersant)

43.5 g of indene (92 wt %; 0.345 mol), 0.7 g of Triton X-100 and 100 ml of water were put into a 500-ml 3-mouthed flask, and mixed by stirring. Mixing was continued at 60° C. as 27.5 g of bromine (0.172 mol, 0.5 mol/mol of indene) was added dropwise over approximately 3 hours. After this, stirring at 60° C. was continued. The reaction mixture was extracted with ethyl acetate directly after dropwise addition of bromine, and after mixing for a further 1 hour. Yields of trans-2-bromoindan-1-ol were calculated from the hydrogen bromide concentrations in the aqueous phase (by gravimetric titration using silver nitrate), and the quantity of indene in the extraction layer was found by GC by means of a calibration line and used to calculate percent conversion.

|  | After adding Br | After mixing for 1 hr |
|---|---|---|
| Indene conversion (%) | 48.7 | 48.5 |
| Yield of product (II) (%) | 30.1 | 40.9 |
| 1,2-dibromoindane (%) remaining | 11.2 | 10.6 |

From the results above the facts below are clear.

1) On mixing at 60° C. for 1 hour after adding bromine approximately 80% of the bromoindane is converted to the intended trans-2-bromoindan-1-ol.

2) The rate of production of 1,2-dibromoindane is extremely rapid because over half of the bromine added is consumed by the end of dropwise addition of bromine.

3) By the end of dropwise addition of bromine approximately 60% of the 1,2-dibromoindane produced has been converted to trans-2-bromoindan-1-ol.

Embodiment 5

Synthesis of 1,2-dibromoindane by bromination of indene, and synthesis of trans-2-bromoindan-1-ol by hydrolysis of this 1,2-dibromoindane/-synthesis of trans-2-bromoindan-1-ol from indene by by-product hydrogen bromide and hydrogen peroxide (added dispersant)

1200 ml of water and 5.6 g of Triton X-100 were put into a 2000-ml 4-mouthed flask, and stirred to form a dispersion. 330.5 g of indene (88 wt %; 2.50 mol) was added and stood overnight. The mixture was then mixed at 60°–70° C. while 200.0 g of bromine (1.25 mol) was added dropwise, requiring 4 hours. The solution became a yellow emulsion which included trans-2-bromoindan-1-ol crystals and indene. After mixing at the same temperature for an hour, 139.0 g of hydrogen peroxide (35 wt %; 1.43 mol) was added dropwise over 3.5 hours. After dropwise addition a slurry formed which included yellow crystals. Mixing was continued at 60° C. for 1 hour, followed by stirring during cooling for 18 hours. 400 ml of dichloromethane was added to the reaction liquor, and after mixing it was filtered under decreased pressure. The cake was washed with 200 ml of water and 160 ml of dichloromethane, and then dried under decreased pressure to obtain 410.6 g of white crystals of trans-2-bromoindan-1-ol (yield 77.1%).

Embodiment 6

Synthesis of 1,2-dibromoindane by bromination of indene, and synthesis of trans-2-bromoindan-1-ol by hydrolysis of this 1,2-dibromoindane/synthesis of trans-2-bromoindan-1-ol from indene by by-product hydrogen bromide and hydrogen peroxide (use of chlorobenzene, added dispersant)

160 ml of water, 60.0 g of indene (95 wt %; 0.49 mol) and 1.12 g of Triton X-100 were put into a 500-ml 3-mouthed flask, and mixed as they were heated to 60° C. 80 ml of chlorobenzene was added, and 41.2 g of bromine (0.258 mol) was added dropwise over 1 hour at 60°–63° C. when the chlorobenzene layer was sampled, diluted with ethyl acetate and analysed by GC, the composition below emerged.

| Component | Composition (GC area %) |
|---|---|
| Indene | 54.4 |
| 1,2-Dibromoindane | 16.7 |
| Trans-2-bromoindan-1-ol | 25.1 |

From the results above it is evident that approximately half of the indene was consumed and approximately 60% of the 1,2-dibromoindane produced by bromination was converted to the desired trans-2-bromoindan-1-ol.

Moreover, on mixing at the same temperature for 2 hours 45 minutes, white crystals of trans-2-bromoindan-1-ol separated out in the chlorobenzene layer. Then 23.5 g of hydrogen peroxide (35 wt %; 0.242 mol) was added at 61°–62° C., which required 1 hour 45 minutes, followed by mixing for a further 2 hours at the same temperature. The reaction mixture was cooled to 30° C., which required ca. 2 hours, being mixed as it cooled. The lower slurry layer was isolated, cooled to 5° C., and then filtered under decreased pressure. The cake was washed with 20 ml of chlorobenzene and then dried under decreased pressure to obtain 81.87 g of white crystals of trans-2-bromoindan-1-ol (yield 78.2%).

Embodiment 7

Synthesis of 1,2-dibromoindane by bromination of indene, and synthesis of trans-2-bromoindan-1-ol by hydrolysis of this 1,2-dibromoindane/synthesis of trans-2-bromoindan-1-ol from indene by by-product hydrogen bromide and hydrogen peroxide (no added dispersant)

160 ml of water and 60.0 g of indene (95 mol%; 0.49 mol) were put into a 500-ml 4-mouthed flask, and mixed as they were heated to 63° C. 40.1 g of bromine (0.25 mol) was added dropwise at 60°–63° C., requiring 30 minutes. On standing, 2 layers separated; the lower layer (organic layer) was transparent pale orange and no crystals could be observed. On mixing for a further 1 hour 15 minutes at 60° C., crystals of trans-2-bromoindan-1-ol were seen in the organic layer. Then 23.55 g of hydrogen peroxide (35 wt %; 0.24 mol) was added dropwise, requiring 25 minutes. After mixing for 3.5 hours at the same temperature, mixing was continued during air cooling overnight. 80 ml of chlorobenzene was added to the reaction mixture which included sticky semi-crystals, and mixed for 30 minutes. The slurry was filtered under decreased pressure at 18° C., and the cake was washed with a small quantity of chlorobenzene, and dried under decreased pressure. 52.14 g of white crystals of trans-2-bromoindan-1-ol (yield 49.9%) was obtained.

Embodiment 8

Synthesis of 1,2-dibromoindane by bromination of indene, and synthesis of trans-2-bromoindan-1-ol by hydrolysis of this 1,2-dibromoindane/synthesis of trans-2-bromoindan-1-ol from indene by by-product hydrogen bromide and hydrogen peroxide (use of ortho-dichlorobenzene, no added dispersant)

100 ml of water and 0.70 g of Triton X-100 were put into a 300-ml 4-mouthed flask, and mixed as 80 ml of ortho-dichlorobenzene and 60.0 g of indene (95 wt %; 0.491 mol) were added. At 20° C., 41.54 g of bromine (0.259 mol) was added with strong stirring and air cooling over approximately 5 minutes. After dropwise addition the temperature of the reaction mixture became 52° C. After mixing at 60° C. for 13 hours, 23.8 g of hydrogen peroxide (35 wt %; 0.245 mol) was added dropwise at the same temperature, requiring 3 hours, followed by mixing for a further 3 hours at 60° C. and then separation into an aqueous layer and a slurry layer. The aqueous layer was extracted with 120 ml of ortho-dichlorobenzene, and the extract layer was bulked with the earlier slurry layer. The warm slurry layer was cooled gradually to 20° C. under stirring, the crystals which came down were isolated by centrifugation and washed with 30 ml of ortho-dichlorobenzene. The wet crystals were dried at 65°–70° C. under decreased pressure to obtain 72.18 g of white crystals of trans-2-bromoindan-1-ol (yield 69.0%).

Embodiment 9

Synthesis of a mixture of 1,2-dibromoindane (I) and trans-2-bromoindan-1-ol (II) by indene-hydrogen bromide-hydrogen peroxide reaction 21.6 g of indene (88 wt %; 0.164 mol), 16.9 g of water, 31.0 g of hydrogen bromide (47 wt %, 0.18 mol) and 9 ml of chlorobenzene were put into a 100-ml 3-mouthed flask and mixed as they were cooled to −10° C. At this time the pH was 4.13. 17.5 g of hydrogen peroxide (35 wt %; 0.18 mol) was added dropwise at −9° to −11° C., requiring 1 hour 15 minutes. At this time the pH was −0.71. After finishing dropwise addition mixing was performed at the same temperature, and the surface area ratio of 1,2-dibromoindane (I) and trans-2-bromoindan-1-ol (II) was traced by HPLC and changes in indene concentration were traced by GC surface areas.

| Time (hr) | 0 | 1.5 | 2.5 | 3.5 | 5.5 |
|---|---|---|---|---|---|
| I:II | 92:8 | 90:10 | 90:10 | 89:11 | 88:12 |
| Indene | 70.0 | 59.0 | 60.0 | 54.9 | 53.3 |

Mixing was continued for 5.5 hours at the same temperature. At this time the pH was −0.31. The temperature was raised to 15° C. over 15 minutes. Mixing was continued for 30 minutes at this temperature and when HPLC and GC analyses were performed the HPLC surface area ratio (I):(II) was 86:14, and the percentage surface area accounted for by indene on GC was 43. When similar analyses were performed after mixing overnight (ca. 13 hours) at 16°–21° C. the HPLC (I):(II) surface area ratio was 82:18 and the percentage surface area of indene on GC was 32%. At this time pH was 1.33. After mixing at 21° C. for 1.5 hours the temperature was raised to 60° C., and on analysis after 3.5 hours the HPLC (I):(II) surface area ratio was 79:21 and the percentage surface area of indene on GC was 25%. When analysed when mixed while cooling from 60° C. the HPLC (I):(II) surface area ratio was 63:37 and the percentage surface area of indene was 13%. The pH at this time was 1.40.

From the results above the following facts are clear.
(1) At −10° C. while pH is low (pH<0) the (I):(II) ratio is almost constant. Indene is also consumed in the reaction. This means that at low temperatures below 0° C. the addition of BrOH and Br$_2$ to indene progresses but the hydrolysis of (II) is extremely slow.
(2) At room temperature hydrolysis proceeds more rapidly than at ≦0° C. As the reaction proceeds the pH rises and the velocity tends to decrease.
(3) At the same pH the velocity of the hydrolysis reaction is markedly greater at 60° C. than at room temperature.

The reaction mixture was filtered under decreased pressure, washed with 5 ml and 10 ml of chlorobenzene and then dried at 40° C. under decreased pressure, to obtain 26.7 g of white crystals of trans-2-bromoindan-1-ol (II) (yield 76.5%). Purity by the GC surface area percentage method was 100.0%.

Embodiment 10

Synthesis of a mixture of 1,2-dibromoindane (I) and trans-2-bromoindan-1-ol (II) by indene-hydrogen bromide-hydrogen peroxide reaction 21.6 g of indene (88 wt %; 0.164 mol), 17.5 g of hydrogen peroxide (35 wt %; 0.18 mol) and 9 ml of chlorobenzene were put into a 100-ml 3-mouthed flask and mixed as they were cooled. At this time the pH was 4.06. 31.0 g of hydrogen bromide (47 wt %, 0.18 mol) was added dropwise at −9° to −11° C. over 1 hour 20 minutes. The surface area ratio of (I) and (II) in HPLC analysis was 95:5, and the surface area percentage of indene in GC was 53. A further 31.0 g of hydrogen bromide (47 wt %, 0.18 mol) was added dropwise over 1 hour 20 minutes at the same temperature. At this time the pH was −0.21. The surface area ratio of (I) and (II) in HPLC analysis was 94:6, and the surface area percentage of indene in GC was 22. On analysis after mixing for 1 hour at the same temperature the HPLC surface area ratio (I):(II) was 94:6, and the percentage surface area accounted for by indene on GC was 2.8. At this time the pH was 0.03. When analyses were performed after mixing overnight the HPLC (I):(II) surface area ratio was 93:7 and the percentage surface area of indene on GC was 2.6.

From the results above the following facts are clear.
1) When the hydrogen bromide concentration is large (when the quantity of water in the system is small) the velocity of the indene addition reactions becomes large.
2) When the hydrogen bromide concentration is large the ratio of the indene addition reaction products (I) and (II) changes, with the percentage of (I) becoming larger.
3) As in Embodiment 9, the hydrolysis of (I) is extremely slow at −10° C.

The reaction mixture was mixed for a further 9 hours at 60° C. and after stirring under cooling overnight the crystals that came down were filtered out under decreased pressure, washed with 5 ml of water and 10 ml of chlorobenzene and then dried at 40° C. under decreased pressure, to obtain 27.3 g of white crystals of trans-2-bromoindan-1-ol (II) (yield 78.1%).

The Possibility of industrial utilization

By means of the present invention trans-2-bromoindan-1-ol can be manufactured industrially cheaply and simply with good yield, by using 1,2-dibromoindane as the starting material.

We claim:

1. Method for making trans-2-bromoindan-1-ol represented by Formula (II)

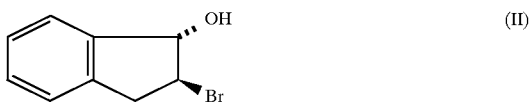

characterized in that 1,2-dibromoindane represented by General Formula (I)

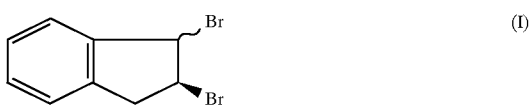

(where the configuration of the bromine atoms on position 1 and position 2 are trans or cis, or a mixture of trans and cis isomers) is hydrolysed.

2. Method for making trans-2-bromoindan-1-ol according to claim 1, characterized in that the aforementioned hydrolysis reaction is performed in the presence of an aprotic organic solvent.

3. Method for making trans-2-bromoindan-1-ol according to claim 2, characterized in that the aforementioned aprotic organic solvent is chlorobenzene.

4. Method for making trans-2-bromoindan-1-ol according to claim 1, characterized in that the aforementioned hydrolysis reaction is performed at 50°–80° C.

5. Method for making trans-2-bromoindan-1-ol according to claim 1, characterized in that the aforementioned hydrolysis reaction is performed in the presence of a dispersant or an emulsifying agent.

6. Method for making trans-2-bromoindan-1-ol according to claim 5, characterized in that the aforementioned dispersant or emulsifying agent is polyoxyethylene-(10) octyl phenyl ether.

7. Method for making trans-2-bromoindan-1-ol according to claim 1, characterized in that the aforementioned 1,2-dibromoindane is synthesized by brominating indene, and this 1,2-dibromoindane is hydrolysed continuously without isolating it.

8. Method for making 1,2-dibromoindane represented by General Formula (I)

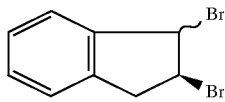
(I)

(where the configuration of the bromine atoms on position 1 and position 2 are trans or cis, or a mixture of trans and cis isomers) by reacting indene with hydrogen bromide in the presence of hydrogen peroxide.

9. Method for making 1,2-dibromoindane according to claim 8, characterized in that water is used as the solvent for the aforementioned reaction.

10. Method for making 1,2-dibromoindane according to claim 8, characterized in that the aforementioned reaction is performed in the presence of an aprotic organic solvent.

11. Method for making 1,2-dibromoindane according to claim 10, characterized in that the aforementioned aprotic organic solvent is chlorobenzene.

12. Method for making 1,2-dibromoindane according to claim 8, characterized in that the aforementioned reaction is performed at −30° C. to 0° C.

13. Method for making 1,2-dibromoindane according to claim 8, characterized in that the aforementioned reaction is performed in the presence of a dispersant or an emulsifying agent.

14. Method for making 1,2-dibromoindane according to claim 13, characterized in that the aforementioned dispersant or emulsifying agent is polyoxyethylene-(10) octyl phenyl ether.

15. Method for making trans-2-bromoindan-1-ol represented by Formula (II)

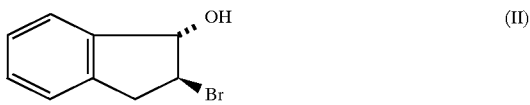
(II)

By reacting indene with hydrogen peroxide and hydrogen bromide in the presence of water.

16. Method for making trans-2-bromoindan-1-ol according to claim 15, characterized in that the aforementioned hydrolysis reaction is performed in the presence of an aprotic organic solvent.

17. Method for making trans-2-bromoindan-1-ol according to claim 16, characterized in that the aforementioned aprotic organic solvent is chlorobenzene.

18. Method for making trans-2-bromoindan-1-ol according to claim 15, characterized in that the aforementioned hydrolysis reaction is performed at 50°–80° C.

19. Method for making trans-2-bromoindan-1-ol according to claim 15, characterized in that the aforementioned hydrolysis reaction is performed in the presence of a dispersant or an emulsifying agent.

20. Method for making trans-2-bromoindan-1-ol according to claim 19, characterized in that the aforementioned dispersant or emulsifying agent is polyoxyethylene(10) octyl phenyl ether.

* * * * *